United States Patent [19]

Marumo et al.

[11] Patent Number: 4,806,143

[45] Date of Patent: Feb. 21, 1989

[54] INDOLEACETIC ACID DERIVATIVES AND APPLICATION THEREOF AS PLANT GROWTH REGULATORS

[75] Inventors: Shingo Marumo, Owariasahi; Masato Katayama, Nagoya; Fumio Futatsuya, Omiya; Mikio Saito, Ageo, all of Japan

[73] Assignee: Nippon Kayaku Kabushiki Kaisha, Tokyo, Japan

[21] Appl. No.: 103,584

[22] PCT Filed: Jan. 7, 1987

[86] PCT No.: PCT/JP87/00010

§ 371 Date: Sep. 3, 1987

§ 102(e) Date: Sep. 3, 1987

[87] PCT Pub. No.: WO87/04157

PCT Pub. Date: Jul. 16, 1987

[30] Foreign Application Priority Data

Jan. 8, 1986 [JP] Japan .................................. 61-1850
Jul. 21, 1986 [JP] Japan ................................ 61-169797

[51] Int. Cl.[4] .................... A01N 43/38; C07D 209/18
[52] U.S. Cl. .......................................... 71/96; 548/494
[58] Field of Search ............................ 548/494; 71/96

[56] References Cited

U.S. PATENT DOCUMENTS 2,701,251 2/1955 Fox et al. ............................ 260/319

OTHER PUBLICATIONS

Chemical Abstracts, vol. 75, No. 34996, p. 428, 1970.
Chemical Abstracts, vol. 103, No. 157620v, p. 437, 1985.
Zazimalova et al., Biologia Plantarum, vol. 27, pp. 114–118, 1985, "Auxin-Binding Site in Wheat Shoots: Interactions Between Indol-3-ylacetic Acid and Its Halogenated Derivatives".
Bruce J. Baldi, Janet Pernise Slovin and Jerry D. Cohen, "Synthesis of $^{14}$C-Labeled Halogen Substituted Indole-3-Acetic Acids", J. of Labeled Compounds and Radiopharmaceutical, vol. XXII, No. 3, pp. 279–285.
Hoffman, et al., "Auxin-Like Activity of Systematically Substituted Indoleacetic Acid", Journal Paper No. J-2035 of the Iowa Agricultural Experiment Station, Project 1110, and Project 1139, pp. 437–441.
Bottger, et al. "Growth of *Avena coleoptiles* and pH Drop of Protoplast Suspensions Induced by Chlorinated Indoleacetic Acids", *Planta* 140, pp. 89–92 (1978).

*Primary Examiner*—David B. Springer
*Attorney, Agent, or Firm*—Banner, Birch, McKie & Beckett

[57] ABSTRACT

An indole derivative represented by the formula:

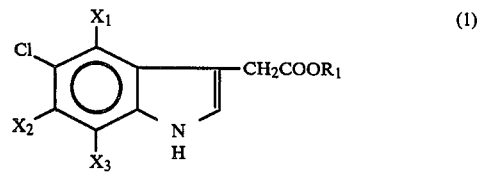

(wherein each of $X_1$, $X_2$ and $X_3$ is a hydrogen or chlorine atom; $X_2$ is a chlorine atom and $X_3$ a hydrogen atom in the case where $X_1$ is a hydrogen atom; $X_2$ is a hydrogen atom and $X_3$ a chlorine atom or a hydrogen atom in the case where $X_1$ is a chlorine atom; and $R_1$ is a hydrogen atom, an alkali metal atom, or a lower alkyl group), a plant growth regulator containing said compound as active ingredient, and a method for regulating plant growth which comprises applying said regulator.

9 Claims, No Drawings

INDOLEACETIC ACID DERIVATIVES AND APPLICATION THEREOF AS PLANT GROWTH REGULATORS

TECHNICAL FIELD

This invention relates to indoleacetic acid derivatives and application thereof as plant growth regulators.

BACKGROUND ART

Conventional indole-3-acetic acid (IAA) and derivatives thereof (methyl indole-3-acetate, indole-3-acetamide, etc.) are disadvantageous in that the carbon atoms at the 2- and 3-positions of indole ring are highly reactive, so that in living plants, these compounds are oxidized, are liable to be decomposed, and disappear in the living plants before they can exhibit their plant-growing action sufficiently.

In addition, 4,7-dichloroindole-3-acetic acid, 5,7-dichloroindole-3-acetic acid, etc. are known in Planta 140, 89 (1978). Therein, it is described that dichloroindole-3-acetic acid above has anti-auxin action, but there is given no description of its ability to promote plant growth.

DISCLOSURE OF THE INVENTION

The present inventor has found that compounds represented by the formula:

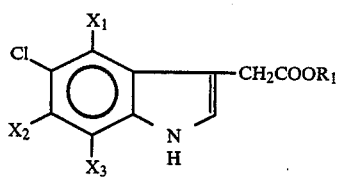

(wherein each of $X_1$, $X_2$ and $X_3$ is a hydrogen or chlorine atom; $X_2$ is a chlorine atom and $X_3$ a hydrogen atom in the case where $X_1$ is a hydrogen atom; $X_2$ is a hydrogen atom and $X_3$ a chlorine atom or a hydrogen atom in the case where $X_1$ is a chlorine atom; and $R_1$ is a hydrogen atom, an alkali metal atom, or a lower alkyl group) are stable in living plants and excellent in plant growth regulating actions, for example, fruiting, fruit-thinning effects and sugar-increasing action, rooting, crop increasing action, wound-healing tissue promoting action in grafted trees, etc.

It cannot be expected at all from the above-mentioned known analogous compounds that although 4,7-dichloroindole-3-acetic acid and 5,7-dichloroindole-3-acetic acid in Planta 140, 89 (1978) above have anti-auxin action on plants, the dichloroindole-3-acetic acid derivatives and trichloroindole-3-acetic acid derivatives represented by the formula (1) of this invention have inverse physiological activities such as rooting effect.

BEST MODE FOR CONDUCTING THE INVENTION

The indoleacetic acid derivative of the formula (1) can be produced, for example, in the following manner.

First, a compound represented by the formula:

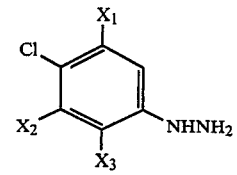

(wherein $X_1$, $X_2$ and $X_3$ have the same meanings as defined above) and a compound represented by the formula:

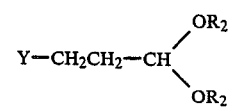

(wherein Y is a cyano group, a carboxyl group or a

group, $R_3$ is a lower alkyl group, and $R_2$ is a methyl group or an ethyl group) are subjected to condensation and ring closure in the presence of a condensation catalyst to obtain a compound represented by the formula:

(4)

(wherein each of $X_1$, $X_2$ $X_3$, Y and $R_2$ have the same meanings as defined above).

Here, the condensation catalyst includes zinc chloride, hydrochloric acid gas-acetic acid, $BF_3$-acetic acid, sulfuric acid-acetic acid, hydrochloric acid-acetic acid, etc., though zinc chloride is preferred. As to the temperature at condensation and ring closure reaction, the reaction is carried out generally at 80° to 200° C., preferably at 100° to 160° C. Although in the above reaction, the compound of the formula (3) can be used as a solvent for reaction, it is also possible to use inert solvents such as hexane, octane and the like which do not react directly with the compound of the formula (3).

In carrying out the above reaction, the compound of the formula (3) and the condensation catalyst are used preferably in amounts in the ranges from 1.1 to 2 moles and 0.5 to 2 moles, respectively, per mole of the compound of the formula (2).

In this invention, the compounds of the formula (2) and the formula (3) are first reacted with each other in the above molar ratio preferably in the presence of an acid catalyst (e.g., camphorsulfonic acid, P-toluene-sulfonic acid, etc.) in a mixed solvent of an inert sovlent (e.g., benzene, toluene, xylene, hexane, etc.) and water (preferably, water: inert solvent = 1:3 to 1:5 by volume), whereby there is isolated a hydrazone compound of the formula:

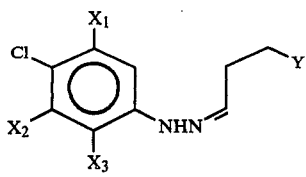

(6)

(wherein each of $X_1$, $X_2$, $X_3$ and Y have the same meanings as defined above), which is then condensed in the presence of the above-mentioned condensation catalyst, whereby the compound of the formula (4) can be obtained.

Next, the compound of the formula (4) obtained by the condensation and ring closure is hydrolyzed, for example, in a solution or a suspension prepared by dissolving or partly suspending an alkali carbonate or alkali metal hydroxide in an alcohol-water mixture, whereby there can be obtained a compound represented by the formula:

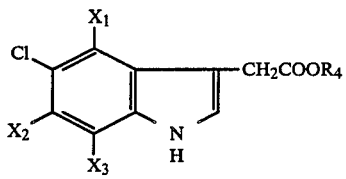

(5)

(wherein each of $X_1$, $X_2$ and $X_3$ have the same meanings as defined above, and $R_4$ is a hydrogen or alkali metal atom).

The hydrolysis reaction is carried out particularly preferably in potassium carbonate in water-alcohol system. As to the temperature at hydrolysis reaction, the reaction is carried out preferably at room temperature to 80° C.

Although the compounds represented by the formula (1) of this invention are applied usually in the form of free acids, alkali metal salts or lower alkyl esters, it is also possible to apply them in the form of amide derivatives or the like which exert the same action as said compounds in their absorption and transfer in living plants.

For applying the compound of the formula (1) of this invention as a plant growth regulator, it can be applied, depending on purpose of use, either as it is or after formulation into a form of composition, e.g., dusts, fine granular formulations, granules, wettable powders, flowable, emulsifiable concentrates, pastes, etc. with the aid of various adjuvants for promoting or stabilizing the effect.

In practice, these various formulations can be applied as it is directly or after dilution to a predetermined concentration with water.

As the adjuvants described herein, there can be exemplified carriers (diluents) and other adjuvants, for example, spreaders, emulsifiers, wetting agents, dispersants, sticking agents, disintegrators, etc.

Liquid carriers include aromatic hydrocarbons such as toluene, xylene and the like; alcohols such as methanol, butanol, glycols and the like; ketones such as acetone and the like; amides such as dimethylformamide and the like; sulfoxides such as dimethyl sulfoxide and the like; methylnaphthalene; cyclohexane; animal and vegetable oils; fatty acids; fatty acid esters; etc.

Solid carriers include clay, kaolin, talc, diatmaceous earth, silica, calcium carbonate, montmorillonite, bentonite, feldspar, quartz, alumina, sawdust, etc.

For the application in the form of pastes, it is sufficient that vaseline, lanolin, various synthetic plastics, rubber, etc. are used as base materials.

As the emulsifiers or the dispersants, surfactants are usually used, and there are exemplified, for example, anionic surfactants, cationic surfactants, nonionic surfactants and ampholytic surfactants, e.g., higher alcohol sodium sulfates, stearyltrimethylammonium chloride, polyoxyethylene alkylphenyl ethers, laurylbetain, etc.

All the compositions can be applied either alone as they are or in admixture with other plant growth regulators. Furthermore, if necessary, they may be mixed with bactericides, insecticides, mitecides, agricultural and horticultural fungicides, soil disinfectants, soil conditioners or nematicides, and can be applied in admixture with fertilizers or herbicides.

The content of the compound of this invention as active ingredient in the plant growth regulator of the present application is varied depending on the type of formulation, application method, and other conditions. Although the compound of this invention may be applied alone, its content is usually in the range of 0.01 to 95% by weight, preferably 0.05 to 50% by weight.

A method for regulating the growth of a plant which is another aspect of this invention, comprises applying the above-mentioned compound usually in an amount in the range from $10^{-6}$ to 2 g in terms of active ingredient for are. For example, for applying said compound in the form of an aqueous solution, an aqueous solution thereof having a concentration of 0.001 to 100 ppm is sprayed in a volume of 0.25 liter to 20 liters per are. In addition, a plant may be immersed in the solution having such a concentration for a definite period of time. When the plant is a young plant or a cutting, it may be transferred to a suitable area for cultivation such as paddy field, upland field or the like after the immersion.

Needless to say, plants to which the present method is applicable include not only crops, for example, principal crops such as rice plant, barly, wheat, oats, rye and the like, potato, sweet potato, taro, vegetables, industrial crops such as mulberry, sugar beet, sugar cane and the like but also plants which participate in the life of human beings in some way or other, for example, forest trees such as cedar, cypress and the like; ornamental plants such as garden trees, flowering plants and the plants such as garden trees, flowering plants and the like; etc.

The application part may be any of the foliage, seed, root, flower, ear and fruit of the above-mentioned plants, and can optionally be selected from them depending on the kind of objective plant and purpose of use.

The term "application" used herein refers to a means which permit absorption of the compound of this invention into a plant and exhibition of its physiological action, for example, spraying, immersion, contact or the like.

The term "plant growth regulating actions" used in this invention means various actions, for example, fruiting and fruit-thinning effects in plants, sugar-increasing action, rooting, wound-healing tissue formation promorting action in grafted trees, increase in crop yield, etc.

In this invention, particularly preferably derivatives are compounds represented by the formula:

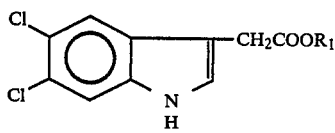

wherein $R_1$ is hydrogen, an alkali metal atom, a methyl group or an ethyl group.

The indoleacetic acid derivatives of this invention are markedly effective particularly with regard to rooting promoting action and yield increasing effect. Therefore, the method for regulating the growth of a plant according to this invention is employed particularly preferably for these two purposes.

EXAMPLES

This invention is explained below with reference to Examples.

SYNTHESIS EXAMPLE 1

Production of methyl 4,5-dichloroindole-3-acetate and n-butyl 5,6-dichloroindole-3-acetate:

With 5.81 g of 3,4-dichlorophenylhydrazine hydrochloride was mixed 11.57 g of 4,4-dimethylbutyric acid, and the resulting mixture was sufficiently stirred to obtain a transparent solution, after which 7.64 g of n-butanol was added. The mixed solution was stirred with treating at 110 C. for 1 hour. The reaction solution was cooled to room temperature, diluted with water, and neutralized with a 1N aqueous sodium hydroxide solution. The aqueous phase was extracted with ethyl acetate, and the ethyl acetate phase was washed with distilled water and a saturated aqueous sodium chloride solution, and dried over anhydrous sodium sulfate. The solvent was removed by distillation and the oily substance thus obtained was purified by a silica gel column chromatography and a silica gel thin-layer chromatography to obtain 0.28 g of methyl 4,5-dichloroindole-3-acetate and 0.395 g of n-butyl 5,6-dichloroindole-3-acetate.

SYNTHESIS EXAMPLE 2

Production of 4,5-dichloroindole-3-acetatic acid:

An aqueous solution prepared by dissolving 120 mg of potassium carbonate in 2.5 ml of water was added to a solution of 44 mg of methyl 4,5-dichloroindole-3-acetate in 5 ml of methanol. The mixture was refluxed for 1.5 hours, after which the methanol was removed by distillation under reduced pressure, and the aqueous solution thus obtained was extracted with ethyl acetate. The aqueous phase was acidified with 1N hydrochloric acid and extracted with ethyl acetate. The ethyl acetate phase was washed with distilled water and a saturated aqueous sodium chloride solution and dried over anhydrous sodium sulfate, and the solvent was removed by distillation under reduced pressure to obtain a crude product. The crude product was purified by a silica gel thin-layer chromatography to obtain 30 mg of 4,5-dichloroindole-3-acetic acid.

SYNTHESIS EXAMPLE 3

Production of 5,6-dichloroindole-3-acetic acid:

An aqueous solution prepared by dissolving 280 mg of potassium carbonate in 2.5 ml of water was added to a solution of 100 mg of n-butyl 5,6-dichloroindole-3-acetate in 10 ml of methanol. After 1.5 hours of refluxing, the methanol was removed from the reaction solution under reduced pressure, and the aqueous solution thus obtained was extracted with ethyl acetate. The aqueous phase was acidified with 1N hydrochloric acid and extracted with ethyl acetate. The ethyl acetate phase was washed with distilled water and a saturated aqueous sodium chloride solution and dried over anhydrous sodium sulfate, and the solvent was removed by distillation under reduced pressure to obtain a crude product. The crude product was purified by a silica gel thin-layer chromatography to obtain 27 mg of 5,6-dichloroindole-3-acetic acid.

M.p. or the analysis results of NMR of the compounds obtained by the processes of Synthesis Examples 1 to 3 are shown below.

TABLE 1

| | | $^1$HNMR (acetone-$d_6$, TMS) ppm |
|---|---|---|
| (1) | 4,5-Dichloroindole-3-acetic acid<br>m.p. 200–203° C. | 7.41 (1H, Singlet)<br>7.39 (1H, Doublet, J=8.4Hz)<br>7.21 (1H, Doublet, J=8.4Hz)<br>3.98 (2H, Singlet) |
| (2) | Methyl 4,5-dichloroindole-3-acetate | 7.42 (1H, Singlet)<br>7.40 (1H, Doublet, J=8.4Hz)<br>7.22 (1H, Doublet, J=8.4Hz)<br>3.99 (2H, Singlet)<br>3.66 (3H, Singlet) |

TABLE 1-continued

| | | |
|---|---|---|
| (3) | [structure: 5,6-dichloroindole-3-acetic acid]<br>5,6-Dichloroindole-3-acetic acid<br>m.p. 189–191° C. | 7.77 (1H, Singlet)<br>7.60 (1H, Singlet)<br>7.40 (1H, Broad Singlet)<br>3.74 (2H, Doublet, J=1Hz) |
| (4) | [structure: methyl 5,6-dichloroindole-3-acetate]<br>Methyl 5,6-dichloroindole-3-acetate | 7.76 (1H, Singlet)<br>7.62 (1H, Singlet)<br>7.41 (1H, Broad Singlet)<br>3.78 (2H, Doublet, J=1Hz)<br>3.65 (3H, Singlet) |
| | | $^1$HNMR (CDCl$_3$, TMS) ppm |
| (5) | [structure: n-butyl 5,6-dichloroindole-3-acetate, CH$_2$COO—n-C$_4$H$_9$]<br>n-Butyl 5,6-dichloroindole-3-acetate | 8.09 (1H, Broad Singlet)<br>7.69 (1H, Singlet)<br>7.45 (1H, Singlet)<br>7.18 (1H, Singlet)<br>4.11 (2H, Triplet, J=6.4Hz)<br>3.70 (2H, Singlet)<br>1.39–1.60 (2H, Multiplet)<br>1.15–1.36 (2H, Multiplet)<br>0.91 (3H, Triplet, J=6.7Hz) |

SYNTHESIS EXAMPLE 4

Production of methyl 4,5,7-trichloroindole-3-acetate:

10.0 Grams (0.047 mole) of 2,4,5-trichlorophenylhydrazine, 9.2 g (0.07 mole) of β-cyanopropionaldehyde dimethylacetal and 7.1 g (0.052 mole) of zinc chloride were mixed and then heated in a nitrogen stream at 140° C. for 2 hours. The reaction mixture was cooled to room temperature and dissolved in an acetic acid-water (2:1) solution, and the resulting solution was extracted with ethyl acetate. The ethyl acetate phase was washed with a saturated aqueous sodium bicarbonate solution, water and then a saturated aqueous sodium chloride solution, and then dried over anhydrous sodium sulfate. The ethyl acetate was removed by distillation under reduced pressure to obtain a black oily substance, which was then purified by a silica gel column chromatography to obtained 0.86 g of the desired compound represented by the formula:

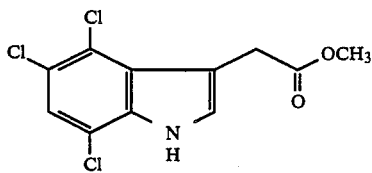

The analysis result of NMR of this compound is shown below.

$^1$H NMR (200 MHz) (CD$_3$)$_2$ CO, TMS) ppm:
7.48 (1H, s) ... C$_2$—H
7.34 (1H, s) ... C$_6$—H
3.99 (2H, s) ... CH$_2$—
3.66 (3H, s) ... OCH$_3$
MS (75 ev) (relative intensity, %)
m/z 295 (M$^+$+4, 10),
293 (M$^+$+2, 23), 291 (M$^+$, 24),
260 (6), 259 (5), 258 (7),
236 (30), 234 (91), 232 (100),
199 (7), 198 (9), 197 (11),
162 (12), 161 (13), 118 (7),
116 (8), 97 (9), 98 (9).

SYNTHESIS EXAMPLE 5

Production of 4,5,7-trichloroindole-3-acetic acid:

An aqueous solution containing 8.4 g (0.15 mole) of potassium hydroxide in 10 ml of water was added to a solution of 4.3 g (0.015 mole) of methyl 4,5,7-trichloroindole-3-acetate in 50 ml of methanol, and the resulting mixture was heated at 50° C. for 10 hours, after which the reaction mixture was concentrated under reduced pressure until it became an aqueous solution. Said aqueous solution was acidified with acetic acid and extracted with ethyl acetate. The ethyl acetate phase was washed with water and a saturated aqueous sodium chloride solution and then dried over anhydrous sodium sulfate, and subsequently the ethyl acetate was removed by distillation under reduced pressure to obtain crude 4,5,7-trichloroindole-3-acetic acid, which was then purified by a column chromatography (silica gel) to obtain 3.3. g of the desired compound represented by the formula:

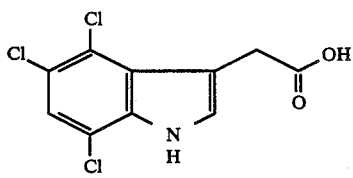

The analysis results of NMR is shown below:
$^1$H NMR (200 MHz) (CD$_3$)$_2$ CO, TMS) ppm
7.50 (1H, s) ... C$_2$—H
7.35 (1H, s) ... C$_6$—H
2 3.99 (2H, s) ... —CH$_2$—
MS (75 ev) (relative intensity, %)
m/z 281 (M$^+$+4, 8),
279 (M$^+$+2, 23), 277 (M$^+$, 25), 236 (40), 234 (88), 232 (100),
199 (11), 198 (10), 197 (16),
162 (16), 161 (16).

SYNTHESIS EXAMPLE 6

Production of an intermediate 2,4,5-trichlorophenylhydrazine:

19.65 Grams (0.1 mole) of 2,4,5-trichloroaniline was cooled to 0° C., after which 75 ml of concentrated hydrochloric acid was added with stirring and the stirring was continued for 30 minuts. With cooling on an ice-salt bath, 25 ml of an aqueous solution containing 7.59 g (0.11 mole) of sodium nitride was added dropwise. After 30 minutes, the diazo solution thus obtained was added to a solution of 45.1 g (0.20 mole) of stannous chloride dihydrate in 75 ml of hydrochloric acid with stirring at 0° C., and the resulting mixture was stirred for another 1 hour. The reaction mixture was made alkaline with a 4 N aqueous sodium hydroxide solution and extracted with ethyl acetate. The ethyl acetate phase was washed with water and a saturated aqueous sodium chloride solution and dried over anhydrous sodium sulfate. The ethyl acetate was removed by distillation under reduced pressure, and then the crude product was purified by a column chromatography (silica gel, eluent: ethyl acetate-n-hexane) to obtain 14.85 g of the desired compound represented by the formula:

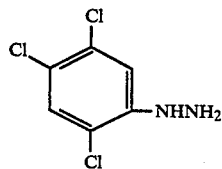

The analysis results of NMR and MS are shown below:

$^1$H NMR (200 MHz) (CDCl$_3$, TMS) ppm
7.29 (1H, s)
7.27 (1H, s)
5.70 (1H, br, s)
3.20 (2H, br, s)
MS (75 ev) (relative intensity, %)
m/z 214 (M+, 32), 212 (M+, 96),
210 (M+, 100), 198 (28), 196 (79),
194 (91), 171 (20), 169 (57),
167 (55), 160 (19), 158 (27), 145 (23),
124 (10), 109 (29), 97 (23), 84 (16),
74 (29), 61 (20).

3,4-Dichlorophenylhydrazine hydrochloride (m.p. 230° C. (decomp.)) used in Synthesis Example 1 can also be synthesized in the same manner as described above.

Next, a more detailed explanation is given below with reference to formulation examples of this inventin, but the kind and mixing ratio of additives are not limited to those described therein but can be selected in wide ranges. In Formulation Examples, all parts are by weight.

FORMULATION EXAMPLE 1 (EMULSIFIABLE CONCENTRATE)

An emulsifiable concentrate is obtained by adding 60 parts of xylene to 25 parts of compound No. (1) to dissolve this compound and mixing therewith 15 parts of a polyoxylethylene alkylphenyl ether and calcium alkylbenzenesulfonate (3:2). This formation is applied after being diluted with water so as to have a concentration of 0.01 to 1%.

FORMULATION EXAMPLE 2 (DUST)

A dust is prepared by adding 95 parts of clay to 5 parts of compound No. (3) and mixing and grinding them. This formulation is applied directly by broadcasting.

FORMULATION EXAMPLE 3 (WETTABLE POWDER)

A wettable powder is obtained by mixing 50 parts of compound No. (3) with 10 parts of a carrier composed of 10 parts of diatomaceous earth and 32 parts of kaolin, homogeneously mixing therewith 8 parts of a mixture of sodium laurylsulfonate and sodium 2,2'-dinaphthylmethanesulfonate, and then grinding the resulting mixture into fine powder. This formulation is applied in the form of a suspension obtained by diluting the preparation with water so as to adjust the concentration to 0.006 to 1%.

FORMULATION EXAMPLE 4 (GRANULES-1)

Granules are obtained by placing 5 parts of fine powder of compound No. (1), 70 parts of clay powder, 20 parts of bentonite as binder, and 5 parts of sodium benzenesulfonate as wetting agent in a suitable mixer, adding a suitable amount of water, granulating the resulting mixture by means of an extrusion granulator, drying the resulting granules, and sieving the same.

FORMULATION EXAMPLE 5 (GRANULES-2)

Granules are obtained by placing 5 parts of fine powder of compound No. (4), 93.5 parts of potassium chloride, 1 part of sodium polyacrylate and 0.5 part of xanthan gum in a suitable mixer, adding a suitable amount of water, granulating the resulting mixture by means of an extrusion granulator, drying the resulting granules, and sieving the same.

EXPERIMENTAL EXAMPLE 1

Avena straight growth promoting effect test (Avena coleoptile straight growth test)

Glumes were removed from seeds of oats (Avena sativa L.), after which the seeds were planted in wetted vermiculite, thereafter covered with vermiculite, irradiated with red light in a growth cabinet at 25° C. for 48 hours, and then incubated therein in the dark for 24 hours. Cutting was conducted as a position about 5 cm about the ground the upper ends were trued up. The upper end of 2 mm in length was removed, after which a piece of 5 mm in length was cut off from the residue, and ten of the pieces thus obtained were floated on 2 ml of each previously prepared test solution contained 0.01 to 0.1 ppm of the compound of this invention or a reference compound in a Petri dish having an inside diameter of 3.5 cm. Fifteen hours after the treatment, the pieces were taken out and their length was measured. The test was carried out in two replications and the average was calculated.

IAA was used at the reference compound. The results are shown in Table 2.

TABLE 2

| | Avena straight-growth test | |
|---|---|---|
| Compound | Concentration ppm | Degree of straight growth (cm) |
| Compound (1) | 0.01 | 0.60 |
| | 0.1 | 0.62 |
| Compound (3) | 0.01 | 0.63 |
| | 0.1 | 0.69 |
| IAA | 0.01 | 0.56 |
| | 0.1 | 0.58 |
| Untreated | — | 0.54 |

EXPERIMENTAL EXAMPLE 2

Promoting action on the formation of adventitious root by a mung beam hypocotyl cutting Mung beans (Vigna ratiata) germinated in a greenhouse were grown at definite temperatures (the lowest 18° C. to the highest 27° C.) for 11 days and when the length of stem reached about 10 cm, the root system having a length of 3 cm or less was removed from the cotyledon and the cotyledon node to prepare cuttings composed of a hypocotyl of 3 cm in length, two primary leaves and a undeveloped 1st true leaf.

The basal portion of each cutting of mung beam thus obtained was immersed in a solution of each compound to be tested having a predetermined concentration (0.1 to 1.0 ppm), and after 7 days, the number of adventitious roots which jutted out from the hypocotyl was investigated. The treatment with agent and the gròwing for 7 days were conducted in an artificial climate chamber previously set at 25° C. The results are shown in Table 3.

TABLE 3

| | The number of adventitious roots from mung bean hypocotyl | |
|---|---|---|
| Compound | Concentration ppm | Degree of straight growth (cm) |
| Compound (1) | 0.1 | 23.0 |
| | 1.0 | 23.0 |
| Compound (3) | 0.1 | 26.2 |
| | 1.0 | 55.2 |
| Compound (4) | 0.1 | 24.1 |
| | 1.0 | 38.2 |
| IAA | 0.1 | 13.0 |
| | 1.0 | 11.8 |
| Untreated | — | 10.6 |

EXPERIMENTAL EXAMPLE 3

Chinese cabbage hypocotyl straight-growth test

Washed seeds of Chinese cabbage were planted on wetted absorbent cotton-filter paper, and grown for 2 days in an artificial climate chamber in which the cycle conditions of high irradiation at 25° C. for 16 hours and dark for 8 hours was mainted. Seedlings having a hypocotyl of about 4 mm in length were placed on filter paper immersed in 3 ml of a previously prepared test solution in a Petri dish having a diameter of 6 cm, and incubated in the dark for 72 hours, and the length of hypocotyl was measured.

The test results were as shown in Table 4 and indicate that the inhibitory effect on hypocotyl straight growth of the compounds of this invention is remarkable as compared with the reference compound IAA.

TABLE 4

| Concentration | $10^{-6}$ mole | $3 \times 10^{-6}$ mole | $10^{-5}$ mole | $3 \times 10^{-5}$ mole | $10^{-4}$ mole |
|---|---|---|---|---|---|
| IAA | 18.4 mm | 19.5 mm | 17.5 mm | 16.1 mm | 16.2 mm |
| Compound (1) | 17.8 | 16.4 | 14.8 | 10.8 | 8.6 |
| Compound (3) | 16.9 | 12.4 | 8.9 | 8.8 | 6.9 |
| Untreated (Water) | 19.7 | | | | |

EXPERIMENTAL EXAMPLE 4

Ripening-improving effect on paddy-rice plant by foliar treatment

A farm land to which paddy-rice plants (cultivar: "Hatsuboshi") had been transplanted on May 4, 1986 was divided so as to adjust the sizes of each division to 2 m×10 m, and on August 9 (initial earing-up), the foliage and ears were sprayed with a 10 ppm aqueous solution of compound (3) of this invention (hereinafter referred to as 5,6-Cl$_2$ IAA) or a 10 ppm aqueous solution of indole-3-butyric acid (hereinafter referred to as IBA) as reference, both containing a spreader (Shin Gramin), in a volume of 1,000 liters/ha. Harvesting was conducted on September 17, and after drying, 20 rice plants were randomly collected from each division and their average weight of ear and percentage of ripened grains were investigated.

The test was carried out in four replications.

The results were as shown in Table 5: the percentage of ripened grains was apparently increased.

TABLE 5

| Ripening-improving effect on paddyrice plant (cultivar: "Hatsuboshi") | | | |
|---|---|---|---|
| Agent tested | Concentration (ppm) | Average weight of ear (g) | Percentage of ripened grains (%) |
| Untreated | — | 1.50 | 78.96 |
| 5, 6-Cl$_2$ IAA | 10 | 1.56 | 87.62 |
| IBA | 10 | 1.50 | 82.22 |

EXPERMENTAL EXAMPLE 5

Yield-increasing effect on wheat by foliar treatment at the time of flowering

A farm land seeded with wheat (cultivar: "Nohrin No. 61") on Nov. 9, 1985 was divided so as to adjust the sizes of each division to 3 m×4 m, and on May 9 (the time of flowering), the foliage and ears were sprayed with a 10 ppm aqueous 5,6-Cl$_2$ IAA solution or a 10 ppm aqueous IBA solution both containing a spreader (Shin Gramin), in a volume of 1,000 liters/ha. After harvesting and drying, 20 wheat plants were collected from each division and the average weight of ear, the total weight of grains per ear, and the total weight of 1,000 grains were investigated. The test was carried out in four replications.

The results were as shown in Table 6: the average weight of ear, the total weight of grains for ear, and the total weight of 1,000 grains were increased by 7 to 8% each. The numbers in parentheses in the table indicate proportions relative to values measured for an untreated group (untreated group =100).

TABLE 6

Yield-increasing effect on wheat
(cultivar: Nohrin No. 61)

| Agent tested | Concentration (ppm) | Average weight of ear (g) | Total weight of grains per ear (g) | Total weight of 1,000 grains (g) |
|---|---|---|---|---|
| Untreated | — | 1.64 (100) | 1.30 (100) | 37.10 (100) |
| 5,6-Cl$_2$ IAA | 10 | 1.77 (108.2) | 1.40 (107.9) | 39.72 (107.1) |
| IBA | 10 | 1.65 (100.6) | 1.30 (100.0) | 35.54 (95.8) |

EXPERIMENTAL EXAMPLE 6

Yield-increasing effect on kidney bean by foliar treatment

A farm land seeded with kidney bears (cultivar: "Taisho-kintoki") on May 25, was divided so as to adjust the sizes of each division to 2 m × 10 m, and on July 24 (the peak of flowering) or August 6 (the end of flowering), the foliage and flowers were sprayed with a 10 ppm aqueous 5,6-Cl$_2$ IAA solution or a 10 ppm aqueous IBA solution both containing a spreader (Shin Gramin), in a volume of 1,000 liters/ha. After 20 kidney bean plants were harvested and dried, there were investigated the number of pods containing ripe beans, the total weight of beans per plant, the number of beans per pod, the total weight of 100 beans, and the percentage of waste beans. The test was carried out in four replications.

The results were as shown in Table 7: in the case of the treatments at the peak of flowering and at the end of flowering, the number of pods containing ripe beans, the total weight of beans per plant, and the total weight of 100 beans were increased, and the percentage of waste beans was reduced.

TABLE 7

Yield-increasing effect on kidney bean (cultivar: "Taisho-kintoki")

| Agent tested | Concentration (ppm) | Number of pods containing ripe beans per plant | Total weight of beans per plant (g) | Number of beans per pod | Total weight of 100 beans (g) | Percentage of waste beans (%) |
|---|---|---|---|---|---|---|
| (Treatment at the peak of flowering) | | | | | | |
| Untreated | — | 12.17 | 18.81 | 2.49 | 62.18 | 3.79 |
| 5,6-Cl$_2$ IAA | 10 | 13.80 | 22.53 | 2.53 | 67.18 | 2.80 |
| IBA | 10 | 13.20 | 19.28 | 2.17 | 64.56 | 3.16 |
| (Treatment at the end of flowering) | | | | | | |
| Untreated | — | 12.10 | 19.34 | 2.47 | 64.54 | 3.05 |
| 5,6-Cl$_2$ IAA | 10 | 13.50 | 22.06 | 2.47 | 66.25 | 2.60 |
| IBA | 10 | 13.30 | 20.28 | 2.38 | 63.98 | 3.93 |

EXPERIMENTAL EXAMPLE 7

Yield-increasing effect on potato by foliar treatment

A farm land seeded with potato (cultivar "Toyoshiro") on April 29 was divided so as to adjust the sizes of each division to 2 m × 10 m, and on June 28 (the time of tuber formation) or July 3 (the time of tuber thickening), the foliage, buds and flowers were sprayed with a 10 ppm aqueous 5,6-Cl$_2$ IAA solution or a 10 ppm aqueous IBA solution both containing a spreader (Shin Gramin), in a volume of 1,000 liters/ha. Twenty previously marked potato plants were harvested from each division and the weight of a potato, the total weight of potatoes per plant, and the total number of potatoes per plant were investigated.

The results were as shown in Table 8: in the case of the treatment at the time of tube formation, the weight of a potato and the total weight of potatoes per plant were increased, while in the case of the treatment at the time of tuber thickening, the weight of a potato, the total weight of potatoes per plant, and the total number of potatoes per plant were increased.

TABLE 8

Yield-increasing effect on potato
(cultivar: Toyoshiro)

| Agent tested | Concentration (ppm) | Weight of a potato (g) | Total weight of potatoes per plant (g) | Total number of potatoes per plant |
|---|---|---|---|---|
| (Time of tuber formation) | | | | |
| Untreated | — | 104.87 | 1241.89 | 11.84 |
| 5,6-Cl$_2$ IAA | 10 | 114.27 | 1371.20 | 12.40 |
| IBA | 10 | 109.13 | 1188.00 | 12.00 |
| Untreated | — | 88.91 | 1341.74 | 14.63 |
| 5,6-Cl$_2$ IAA | 10 | 104.24 | 1580.56 | 17.78 |
| IBA | 10 | 91.70 | 1407.30 | 13.50 |

EXPERIMENTAL EXAMPLE 8

Rooting-promoting effect on gum tree

Cuttings were prepared by cutting a branch of Indian gum tree (Ficas elastica Roxb.) so that each piece obtained thereby might have two nodes, and cutting down leaves attaching to the respective nodes into half perpendicularly to the costa. The lower cut end of each cutting was soaked in water for 24 hours, after which the cutting was immersed in 0.1, 1 or 10 ppm of 5,6-Cl$_2$ IAA or IBA for 3 hours and washed with water, and then said cut end was soaked in water. The cuttings were cultivated in a greenhouse for 3 weeks while keeping said cut end in contact with water, and then the number of struck roos was investigated.

The test was carried out in ten replications and the average was calculated.

The results were as shown in Table 9: the number of struck roots was increased with an increase of the concentration.

TABLE 9

Rooting-promoting effect on gum tree

| Agent tested | Concentration (ppm) | Number of struck roots | Maximum length of root (cm) |
|---|---|---|---|
| Untreated | — | 3.5 | 0.82 |
| 5,6-Cl$_2$ IAA | 0.1 | 5.2 | 0.83 |
|  | 1 | 8.7 | 0.80 |
|  | 10 | 10.3 | 0.75 |
| IBA | 0.1 | 3.3 | 0.80 |
|  | 1 | 4.5 | 0.79 |
|  | 10 | 5.5 | 0.84 |

INDUSTRIAL APPLICABILITY

Since the indoleacetic acid of this invention is chemically stable and has a good plant-growth-regulating action, it is applicable as a plant growth regulator in various fields.

We claim:

1. An indole derivative represented by the formula:

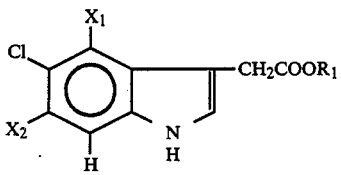
(1)

wherein each of $X_1$, and $X_2$ is a hydrogen or chlorine atom; $X_2$ is a chlorine atom in the case where $X_1$ is a hydrogen atom; $X_2$ is a hydrogen atom in the case where $X_1$ is a chlorine atom; and $R_1$ is a hydrogen atom, an alkali metal atom or a lower alkyl group.

2. An indoleacetic acid derivative according to claim 1, which is represented by the formula:

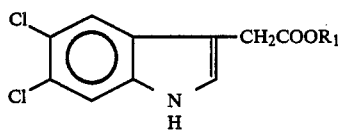

wherein $R_1$ is a hydrogen atom, an alkali metal atom, a methyl group, or an ethyl group.

3. An indoleacetic acid derivative according to claim 2, which is represented by the formula:

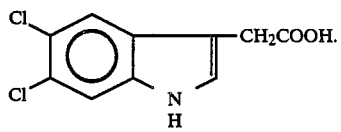

4. A plant growth regulator containing as active ingredient an indole derivative represented by the formula:

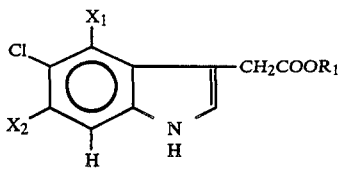
(1)

wherein each of $X_1$, and $X_2$ is a hydrogen or chlorine atom; $X_2$ is a chlorine atom in the case where $X_1$ is a hydrogen atom; $X_2$ is a hydrogen atom in the case where $X_1$ is a chlorine atom; and $R_1$ is a hydrogen atom, an alkali metal atom, or a lower alkyl group.

5. A plant growth regulator according to claim 4, wherein the plant growth regulator is an agent for promoting rooting of plant and for increasing the yield of crops.

6. A plant growth regulator according to claim 4 or 5, wherein the active ingredient is a compound represented by the formula:

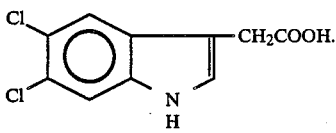

7. A plant growth regulator according to claim 4, wherein the plant growth regulator is an agent for promoting rooting of plants.

8. A method of using, for regulating plant growth, an indole derivative represent by the formula:

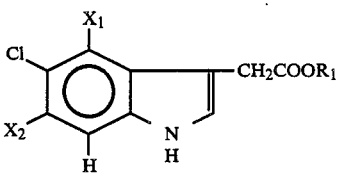
(1)

wherein each of $X_1$, and $X_2$ is a hydrogen or chlorine atom; $X_2$ is a chlorine atom in the case where $X_1$ is a hydrogen atom; $X_2$ is a hydrogen atom in the case where $X_1$ is a chlorine atom; and $R_1$ is a hydrogen atom, an alkali metal atom, or a lower alkyl group 9. A method according to claim 8, wherein the regulation of plant growth is intended to root plants.

* * * * *